United States Patent [19]

Nomura

[11] Patent Number: 4,806,246
[45] Date of Patent: Feb. 21, 1989

[54] PORE SIZE CONTROL USING PLASMA POLYMERIZATION TECHNIQUES

[75] Inventor: Hiroshi Nomura, Minnetonka, Minn.

[73] Assignee: Applied Membrane Technology, Inc., Minnetonka, Minn.

[21] Appl. No.: 850,953

[22] Filed: Apr. 11, 1986

[51] Int. Cl.⁴ ............................................. B01D 13/00
[52] U.S. Cl. ................................ 210/651; 210/321.89; 210/500.23; 210/490; 264/22
[58] Field of Search .................... 210/490, 491, 500.38, 210/653, 500.37, 651, 321.89, 500.23; 264/22; 427/244, 245, 246

[56] References Cited

U.S. PATENT DOCUMENTS

| | | | |
|---|---|---|---|
| 3,228,876 | 1/1966 | Mahon | 210/653 X |
| 3,847,652 | 11/1974 | Fletcher et al. | 210/500.37 X |
| 4,330,406 | 5/1982 | Sano et al. | 210/500.38 X |
| 4,347,139 | 8/1982 | Hayashi | 210/500.37 |

Primary Examiner—Frank Spear
Attorney, Agent, or Firm—Orrin M. Haugen; Thomas J. Nikolai

[57] ABSTRACT

A hydrophobic microporous membrane substrate can be coated with a plasma polymerizate coating in order to reduce the pore size of the substrate to a size smaller than the original pore size but not less than about 10 A. By selecting the particular plasma polymerizate coating, the surface of the substrate may be rendered either hydrophilic or hydrophobic, while the body of the substrate retains the substrate's original properties of mechanical strength and chemical resistance. Three different methods of applying plasma polymer coatings by plasma polymerization techniques are disclosed. These membranes are suitable for separating particulate larger than about 10 A from solutions. These membranes in the form of hollow fibers can be incorporated into separatory modules.

55 Claims, 5 Drawing Sheets

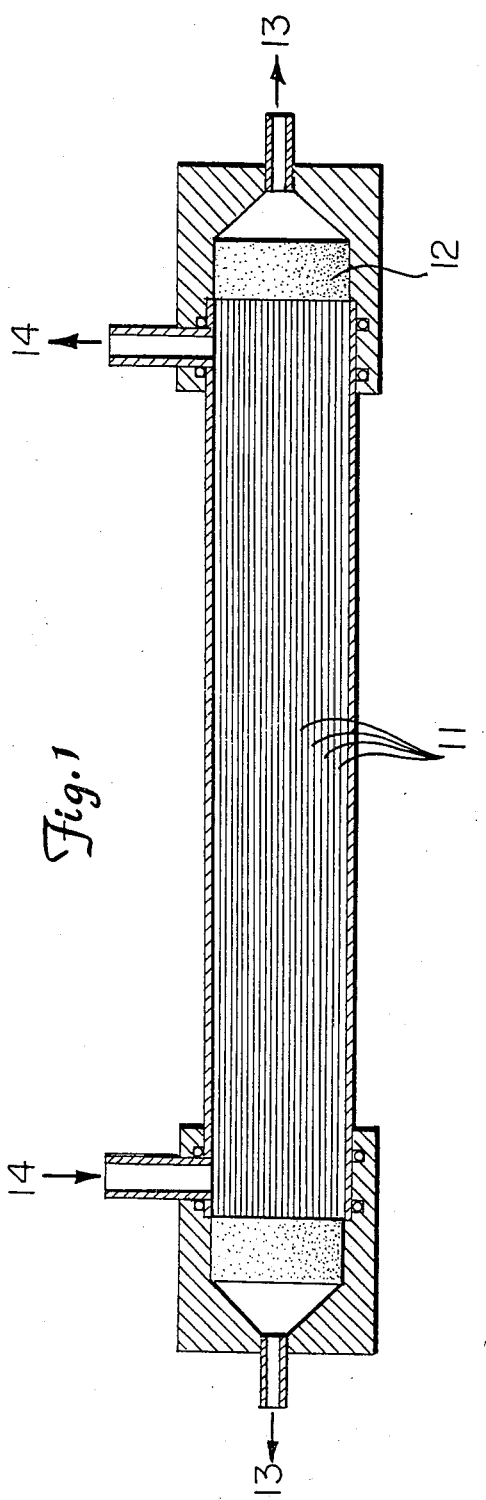
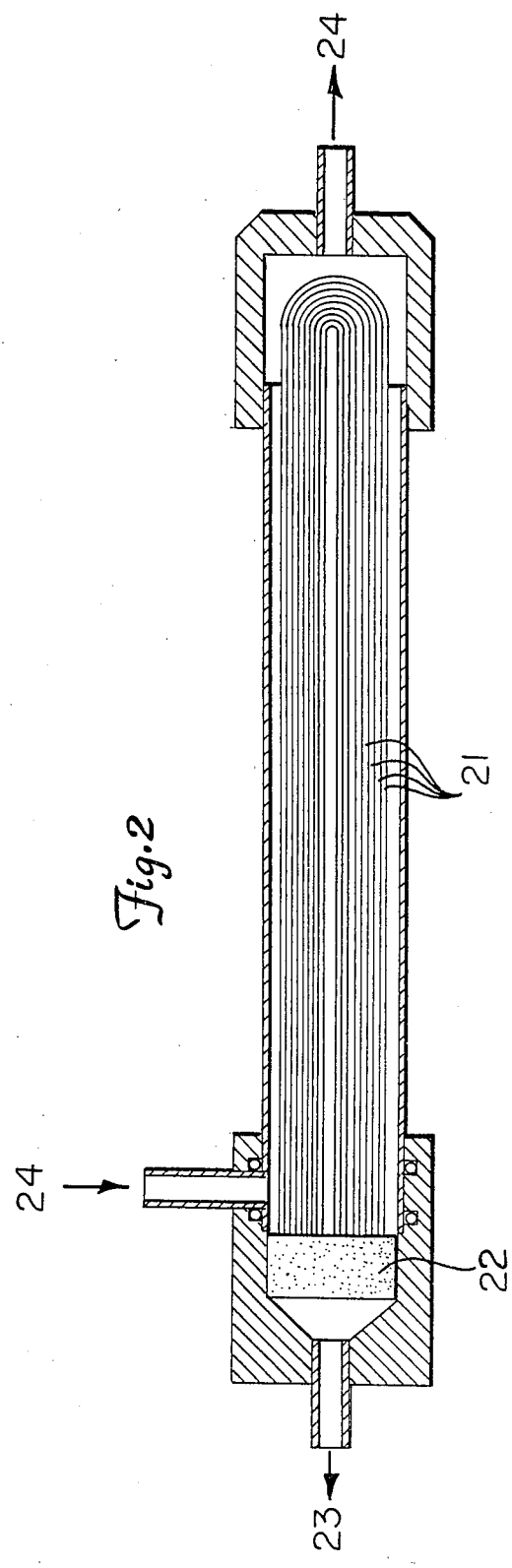

PORE SIZE CONTROL USING PLASMA POLYMERIZATION TECHNIQUES

FIELD OF THE INVENTION

This invention relates to microporous hydrophobic membranes which have been coated with a plasma polymer in order to reduce the pore size of the membrane substrate to a size no smaller than about 10 A. There are three types of plasma polymerizate coatings which may be deposited on the membrane substrate to effect the desired pore size reduction.

Also provided by this invention is a process for preparing these microporous composite membranes of reduced pore size by depositing on the surface of the microporous hydrophobic membrane substrate a plasma polymerizate coating which will effect the desired pore size reduction. There are three types of plasma polymerizate depositions, each relating respectively to the three types of plasma polymerizate coatings.

Further, this invention is directed to a method of using these microporous composite membranes of reduced pore size for separating, concentrating or purifying particles of above about 10 A in size from solutions thereof, and to a separatory module utilizing the present reduced pore size composite membranes, in the form of hollow fibers, to effect such separations. When the particles are plant, mammalian or microbial cells, the disclosed module may be used for culturing, concentrating or purifying such cells or cellular components.

BACKGROUND OF THE INVENTION

Separatory membrane fabrication currently demands the preparation of microporous separatory membranes having such exacting specifications as ultra-fine pore size with a lower limit of about 10 A, resistance to degradation by chemicals, pressure and heat, and specific surface characteristics of hydrophobicity and hydrophilicity. The search to find such specific materials for each individual separatory purpose has often led to expensive and complicated fabrication procedures.

According to the investigations of this invention, by using hydrophobic microporous membranes as the base substrate, plasma polymerization deposition techniques can create novel ultrafiltration membranes which satisfy such precise requirements. Usually, hydrophobic microporous membranes, of the type used as the base substrate for preparing the novel ultrafiltration membranes of this invention, have large pores, in the range of at least about 200 A to at most about 6000 A. While these currently available membranes have a high resistance to chemicals, heat and pressure, due to their simpler polymeric structure, as compared to conventional ultrafiltration membranes, they are not suitable for ultrafiltraton purposes because of molecular weight cutoff due to their unacceptably high pore size.

By controlling the deposition of a plasma polymer, the pore size of these hydrophobic microporous membranes can be reduced from their original size to any specifically required smaller size, down to a lower limit in the range of about 10 A. Because the plasma polymer deposited layer is extremely thin (in the range of 1200 A or less), the membrane substrate retains its porous character, without any significant decrease in the permeabilities of liquids and gases, but with an increased ability to separate ultra-fine particulate from solution.

Conventional plasma polymerization coating techniques, as applied to the fabrication of composite membranes, have all suffered from certain inherent disadvantages, regardless of the type of reactor systems utilized (i.e., Bell Jar reactors, A.F. tandem systems, R.F. coil-inductively coupled tubular reactors). These disadvantages, generally, are due to the fact that such conventional plasma polymerizations involved deposition of the polymer onto a substrate in situations where the energy density of the plasma, and thus the uniformity of the polymer deposition, could not be easily controlled. These disadvantages can generally be summarized as follows:

1. Non-uniformity in plasma polymer deposition rates and plasma polymer coating composition, primarily dependent on the substrate's position in the reactor.
2. Low deposition rates due to low energy density levels leading to very slow membrane production rates. Low energy density levels are encountered with conventional plasma reactors, whether of the Bell Jar or R.F. coil-inductively coupled tubular type, where polymer deposition takes place in the "after glow" zone, or of the A.F. type, where polymer deposition takes place in the glow zone. Low deposition rates in conventional reactors can further be attributed to the build up of plasma coating of the internal electrodes.
3. Inability to evenly and effectively coat multiple membrane substrates, due to competitive shading from the plasma glow, and due to the fact that polymer deposition rates are primarily dependent on the precise position of the substrate in the reactor.
4. Non-uniformity in coating around the exterior of the membrane substrate, for example, around the circumference of a fiber.
5. Problems in the undesirable formation of multiple chemical species, and the inability of efficiently remove waste chemical species.
6. Difficulty in controlling all of these plasma deposition reaction parameters, particularly in scale-ups to commercial production.

This inventor has now unexpectedly discovered that the use of an R.F. capacitively coupled tubular reactor, specifically controlled in terms of system operation, results in plasma polymer deposition techniques, that are highly reliable, able to operate at high production rates, and produce a highly desirable uniform product. According to the process of this invention, the plasma polymer is deposited on the microporous membrane substrate moving through the energy-intensive glow zone in the region between the electrodes of the reactor. It is well known in the art that microporous membrane substrates are extremely difficult to plasma coat due to their sensitivity to manipulative stresses, such as temperature, pressure, tension, and chemical attack. However, this inventor now unexpectedly discloses that microporous membrane substrates can be plasma coated in this manner with speed and efficiency and with uniform desirable results.

BRIEF DESCRIPTION OF THE DRAWINGS

FIG. 1. A separatory module of the both end open type.

FIG. 2. a separatory module of the one end open type.

SUMMARY OF THE INVENTION

Figure 3:
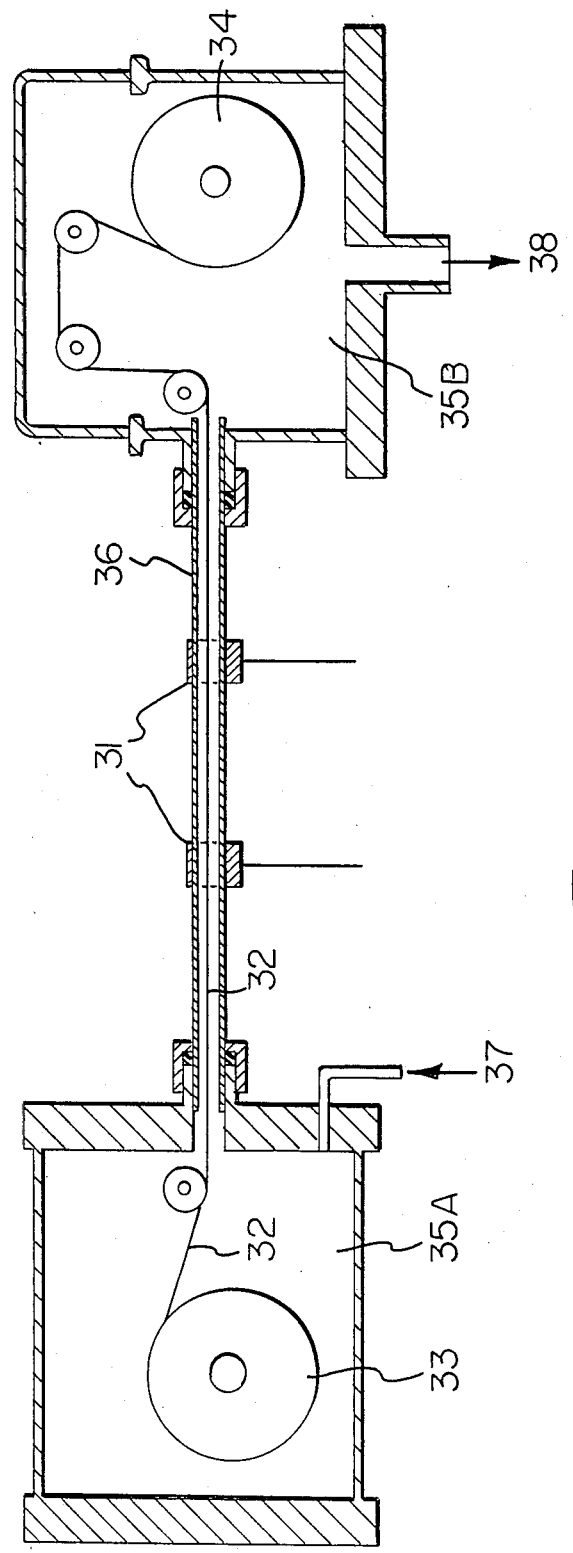
FIG. 3. An outline sectional view of an R.F. plasma polymerization system.

This invention provides microporous composite membranes of reduced pore size and specific surface characteristics of hydrophobicity and hydrophilicity, and a novel method of preparing them, which involves depositing a plasma polymerizate coating of specifically selected monomers onto a hydrophobic microporus membrane substrate.

The hydrophobic microporous membrane substrates which provide the basis for the microporous membranes of reduced pore size of the present invention can be polyolefinic and fluorinated polyolefinic and can be in the form of films, hollow fibers and the like.

The plasma polymerizate coating provides three different classes of reduced pore size microporous membranes as follows:

(i) The deposition of a hydrophobic plasma polymerizate coating onto a hydrophobic microporous membrane substrate, wherein the polymerizate is derived from a low molecular weight aliphatic hydrocarbon monomer.

(ii) The deposition of a hydrophilic plasma polymerizate coating onto a hydrophobic microporous membrane substrate, wherein the polymerizate is derived from a low molecular weight aliphatic amine monomer.

(iii) The deposition of a hydrophilic plasma polymerizate coating onto a hydrophobic microporous membrane substrate, wherein the polymerizate is derived from a low molecular weight aliphatic hydrocarbon monomer admixed with a non-polymerizable plamsa gas.

When the substrate is a hollow fiber, the plasma polymerization may be carried out in an audio frequency powered Bell Jar reactor as further described below. When the substrate is a flat film or hollow fiber, the plasma polymerization may be carried out in either an audio frequency powered Bell Jar reactor, or in a radio frequency powered tubular reactor, as further described below.

Further, according to this invention, the separation of particles larger than about 10 A in size from solutions thereof can be accomplished by incorporating the present novel reduced pore size composite membranes, in the form of hollow fibers, in a separatory module, suitably according to the type shown in FIGS. 1 and 2. The modules as shown in FIGS. 1 and 2 may also serve as an environment for culturing, concentrating or purifying plant, mammalian and microbial cells or cellular products in solutions thereof.

DETAILED DESCRIPTION OF THE INVENTION

Ultrafiltration membranes are presently demanded, for separations from solution of particulate as small as about 10 A. For example, in the area of biotechnology, such membranes are required for the in vitro culturing of living cells in nutrient media, and for concentrating, purifying and separating living cells, microorganisms, proteins, etc., from solutions thereof. Reduction of pore size in microporous membranes by the use of plasma polymerization coating, as developed by this inventor, is extremely useful for the preparation of "tailor made" ultrafiltration membranes for use in such areas, which have desirable surface characteristics, i.e., hydrophobic or hydrophilic, a desired pore size distribution, and resistance to heat, chemicals and pressure.

As disclosed by this inventor, these different classes of reduced pore size, microporous composite membranes can be prepared according to these conditions:

(i) A hydrophobic plasma polymerizate coating is deposited onto a hydrophobic microporous memberane substrate, wherein the polymerizate is derived from a low molecular weight aliphatic hydrocarbon monomer, to provide a microporous composite membrane of reduced pore size and hydrophobic surface characteristics.

(ii) A hydrophilic plasma polymerizate coating is deposited onto a hydrophobic microporous membrane substrate, wherein the polymerizate is derived from a low molecular weight aliphatic amine monomer, to provide a microporous composite membrane of reduced pore size and hydrophilic surface characteristics.

(iii) A hydrophilic plasma polymerizate coating is deposited onto a hydrophobic microporous membrane substrate, wherein the polymerizate is derived from a low molecular weight aliphatic hydrocarbon monomer admixed with a non-polymerizable plasma gas, to provide a microporous membrane of reduced pore size and hydrophilic surface characteristics.

The hydrophobic microporous membranes which may serve as the substrate membranes according to the present invention are all well known and readily commercially available. Suitable substrate membranes may be used in the form of films, hollow fibers and the like. Hollow fibers are a form presently preferred, because a larger area for permeation can be obtained in a specific cubic volume through the use of hollow fibers. Therefore, a separatory device, such as the modules according to the present invention, when employing hollow fibers as the separatory membrane, become more compact. These substrate membranes may be made of polyolefins, such as polyethylene and polypropylene, and fluorinated polyolefins, such as fluorinated ethylene propylene. The substrate membranes suitable for use in this invention have pore sizes in the range of at least about 200 A to at most about 6000 A. The pores are of various shapes according to the method of fabrication and are generally oval or circular. When the pores are non-circular, the minor axis of the smallest pores are at least about 200 A and the major axis of the largest pores are at most about 6000 A. Suitable membrane substrates that meet these requirements are readily commercially available from Mitsubishi Rayon Co. Ltd., under the proprietary names of KPF 190 M, 270 B and 360 A, and EHF 270 W, 270 T, 270 H, 410 C, 390 C and 390 A, and from Celanese Corp., under the proprietary names of CELGARD 2400, 2402, 2500, 2502, 4400, 4410, 4500, 4510, K-442, K-443, X-10 and X-20. Other acceptable polyolefinic and fluorinated polyolefinic films and hollow fibers which may be used are further described in U.S. Pat. Nos. 3,558,764, patented Jan. 26, 1971, 3,679,538, patented July 25, 1972, 3,801,404, patented Apr. 2 1974, 3,801,692, patented Apr. 2, 1974, 3,839,240, patented Oct. 1, 1974, 3,839,516, patented Oct. 1 1974, 3,843,761, patented Oct. 22, 1974, 3,920,785, patented Nov. 18, 1975, 4,058,582, patented Nov. 15, 1977, 4,138,549, patented Feb. 6, 1979, 4,255,376, patented Mar. 10, 1981, 4,257,997, patented Mar. 24, 1981, 4,290,987, patented Sept. 11, 1981 and 4,405,688, patented Sept. 20, 1983, all of which are specifically incorporated herein by reference.

The low molecular weight aliphatic hydrocarbon monomer precursors which may be used in preparing the reduced pore size membranes according to procedures (i) and (iii) above may be, for example, alkanes of up to about 4 carbon atoms, such as methane and ethane, and alkenes of up to about 4 carbon atoms, such as ethylene, propylene, 1-butene and 2-butene. The low molecular weight aliphatic amine monomers, which may be used in preparing the reduced pore size membranes according to procedure (ii) above, may be, for example, triethylamine and allylamine.

The non-polymerizable plasma gas which may be admixed with a monomer, according to procedure (iii), may be nitrogen, oxygen, water or air. The admixture of a non-polymerizable plasma gas with the low molecular weight aliphatic hydrocarbon monomer precursor changes the surface characteristics of the plasma polymer coating from hydrophobic to hydrophilic. Presently, nitrogen is the preferred gas to be used.

The present plasma polymerization involves activating a monomer precursor within the glow zone so as to energize the monomer precursor into a high energy, dissociated form enriched with radicals, electrons and ions (i.e., a plasma) and depositing a plasma polymer thereof onto the surface of the substrate moving through the glow zone. In practice, two different types of plasma reactors may be used. In plasma coating hollow fibers, an audio frequency reactor may be used wherein an electric discharge from an A.F. generator is applied to the internal electrodes of a directly coupled Bell Jar reactor. In plasma coating films or hollow fibers, a radio frequency reactor may be used, wherein an electric discharge from an R.F. generator is applied to the external electrodes of the capacitively coupled tubular plasma reactor. The monomer precursor alone, according to procedures (i) or (ii) or admixed with a non-polymerizable gas, according to procedure (iii), is introduced into the reactor and energized into a plasma. By careful control of system parameters, the monomeric plasma is maintained in the energy-intensive glow zone between the electrodes. The monomer is progressively polymerized, forming a plasma polymer coating on the surface of the microporous membrane substrate moving through the region of the glow zone of the plasma reactor.

The movement of the substrate through the region of the plamsa glow zone is, of course, regulated by both the pulling speed and by the tension on the substrate. Since the plasma glow zone is the region of highest energy density in the plasma reactor, the pulling speed and the tension must be regulated together in order to allow the substrate to have a residence time in the glow zone sufficient to allow proper deposit of plasma polymer to effect the desired pore size reduction, while avoiding any damage to the substrate from the intensity of the glow zone. At the same time, the pulling speed and the tension must be so regulated together as to avoid allowing the substrate to touch either the walls of the reactor or other substrates, as when a plurality of substrates are being coated simultaneously.

Previous investigators have particularly avoided coating polymeric substrates in the region of the R.F. inductively coupled plasma glow zone, because they have experienced uncontrollable degradation of the substrate, and have resorted to coating adjacent to, but outside of, the glow zone. In plasma coatings in A.F. plasma reactors, the electrodes are spaced too far apart, resulting in slow deposition rates, since the energy of the glow zone is diminished by distribution over a larger area. Also, the effectiveness of internal electrodes in previous systems is decreased over time, as plasma polymer coating continues to build up on the electrodes. By close control of the specific variables outlined herein, this inventor has unexpectedly been able to contain accurately controllable and completely reproducible coating of microporous membrane substrates to effect pore size reduction thereof to a specifically requied size.

A suitable R.F. plasma reactor system for the continuous production of microporous microfiltration membranes of reduced pore size, in the form of films or hollow fibers, according to this invention is schematically illustrated in FIG. 3. The R.F. plasma reactor is a tube type reactor 36 with a pair of capacitively coupled external electrodes 31, positioned at either end of the reactor 36, and externally coupled to a radio frequency generator. The highest energy density is maintained in the area between the electrodes 31, that is, the plasma glow zone by controlling both the current from the R.F. generator and the monomer flow rate. If the monomer flow rate is too fast, the glow zone will "spill over" to the region outside the electrodes. If too slow of a monomer flow rate is used, the plasma will fail to ignite or will fail to fill the entire inter-electrode region. The two chambers 35a and 35b are vacuum chambers connected with the reactor 36 in continuous vacuum-sealed relationship therewith, and 38 is an outlet to the vacuum pump. The reactor 36 may be formed of any material with sufficient resistance to withstand the plasma treatment conditions. Presently, quartz, PYREX TM and VYCTOR TM has been found to be satisfactory. In operation, the hollow fiber 32 is continuously traveled through the reactor 36 from the unwind spool 33 to the take-up spool 34. The desired monomer, previously admixed with a non-polymerizable gas if required, is fed into the system through the feed inlet 37. The plasma polymer deposition takes place on the substrate membrane traveling through the region of the plasma glow zone, between the electrodes 31.

Figure 4:
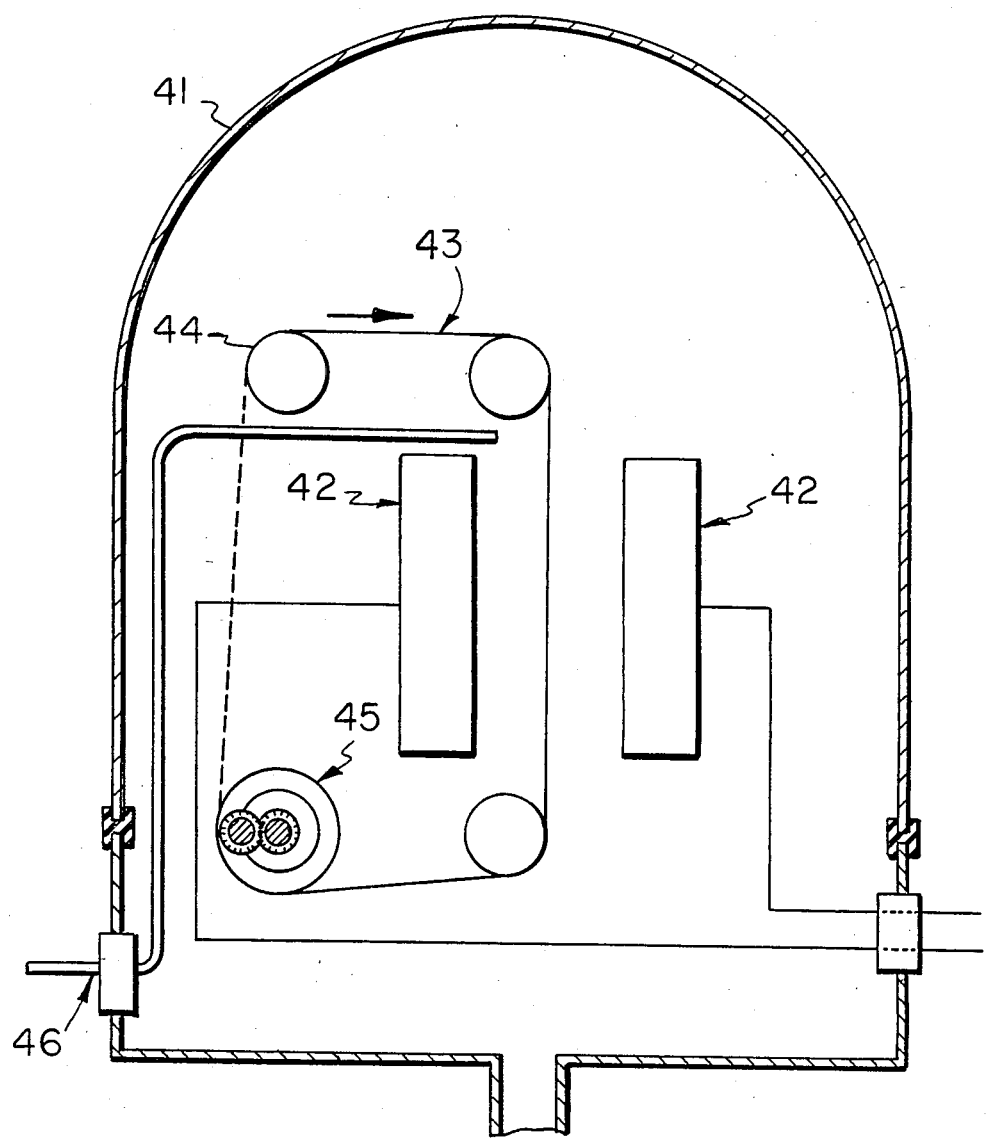
FIG. 4. An outline sectional view of an A.F. plasma polymerization system.

A suitable system for the continuous production of hollow fiber membrane in an A.F. plasma reactor is schematically illustrated in FIG. 4. The A.F. plasma reactor is a Bell Jar reactor 41 with a pair of flat plate electrodes 42 positioned parallel to each other and directly coupled to an external audio frequency power amplifier via high voltage cables. The current from the generator and the monomer flow rate are both controlled so as to maintain the highest energy density in the area between the electrodes 42, that is, the plasma glow zone. The Bell Jar 41 is a vacuum chamber and 47 is an outlet to the vacuum pump. In operation, the hollow fiber or flat film 43 is continuously traveled through the plasma glow zone in the area between the electrodes 42 from the unwind spool 44 to the take-up spool 45. It is to be understood that the direction of travel of the substrate between the electrodes may be in either direction, and thus, the operation of the spools 44 and 45 may be reversed if desired. The monomer, optionally admixed with a non-polymer forming gas, is fed into the system through the feed inlet 46. In the preparation of hollow fiber according to this invention, the R.F. reactor system, described above with reference to FIG. 3, is the presently preferred system due to its efficiency of operation in continuous production.

It is important to minimize the residence time in the plasma glow zone and to keep the substrate as cool as possible (i.e., close to ambient room temperature) to prevent damage to the temperature sensitive substrate. To achieve the desired thickness of plasma polymer coating, the substrate may be passed several times through the glow zone. A system can be provided which reverses the direction of travel of the substrate, allowing a continuous length of substrate to pass through the glow zone several times to achieve the desired plasma polymer coating. The direction of flow of the monomer feed can be either with or against the direction of motion of the substrate through the glow zone.

The energy densities generated in the glow zone of the plasma generator systems according to this invention are much higher than those available with conventional plasma reactors. This requires that the length of exposure to the plasma glow zone be minimized in order to avoid damage to the membrane substrate. For example, a polyolefinic substrate must be moved through the plasma glow zone at a rate normally in excess of about 0.7 cm/sec. for each pass. By passing the substrate through the glow zone multiple times, thicker coatings may be prepared as required. The residence time within the plasma glow zone will, of course, vary with particular substrates. With a more temperature resistant substrate, it is possible to have exposure for a longer period of time in order to achieve the desired plasma polymer coating.

The method of this invention allows for easy deposition of the required plasma polymer coating onto even surfaces, such as films, onto circumferential or convoluted surfaces, such as hollow fibers or uneven membrane substrates, and onto a plurality of substrates, for example, films, or hollow fibers, moving simultaneously through the plasma glow zone. This is because in the present system, the plasma glow zone is able to be maintained at an even density across the cross-sectional area of the tubular reactor. In conventional plasma reactors, even with those which do allow for plasma deposition onto a substrate within the glow zone (e.g., A.F. tandem systems), the glow zone cannot be maintained at high energy density. Also, internally positioned electrodes, of either conventional A.F. or R.F. reactor systems, eventually become coated with plasma polymer over time, further diminishing the energy intensity of the glow zone. In plasma reactors where deposition takes place in the "after glow" zone (e.g., Bell Jar and R.F. coil-inductively coupled tubular reactors), the density of the plasma, and thus the rate of the deposited polymer, decreases with the distance from the plasma glow and the gas flow patterns become uncontrollable. Also, in conventional plasma reactors, the substrate must be specifically positioned, for example, on the electrode or on the wall of the reactor. When such conventional systems, the composition and uniformity of the deposited plasma polymer is known to vary with the position of the substrate relative to the plasma glow. Thus, when multiple substrates are plasma polymer coated simultaneously, the composition and the uniformity of the plasma polymer coating will vary dependant on the individual substrate's position relative to the glow zone. Also, in order to replicate a particular plasma polymer coating onto a particular substrate, the substrate must be carefully positioned in the exact same position within the reactor. In the present system, quality and uniformity of the product within each run and between runs is assured due to the even density throughout the glow zone, and the ability to maintain the high energy level of the glow zone.

Figure 5:
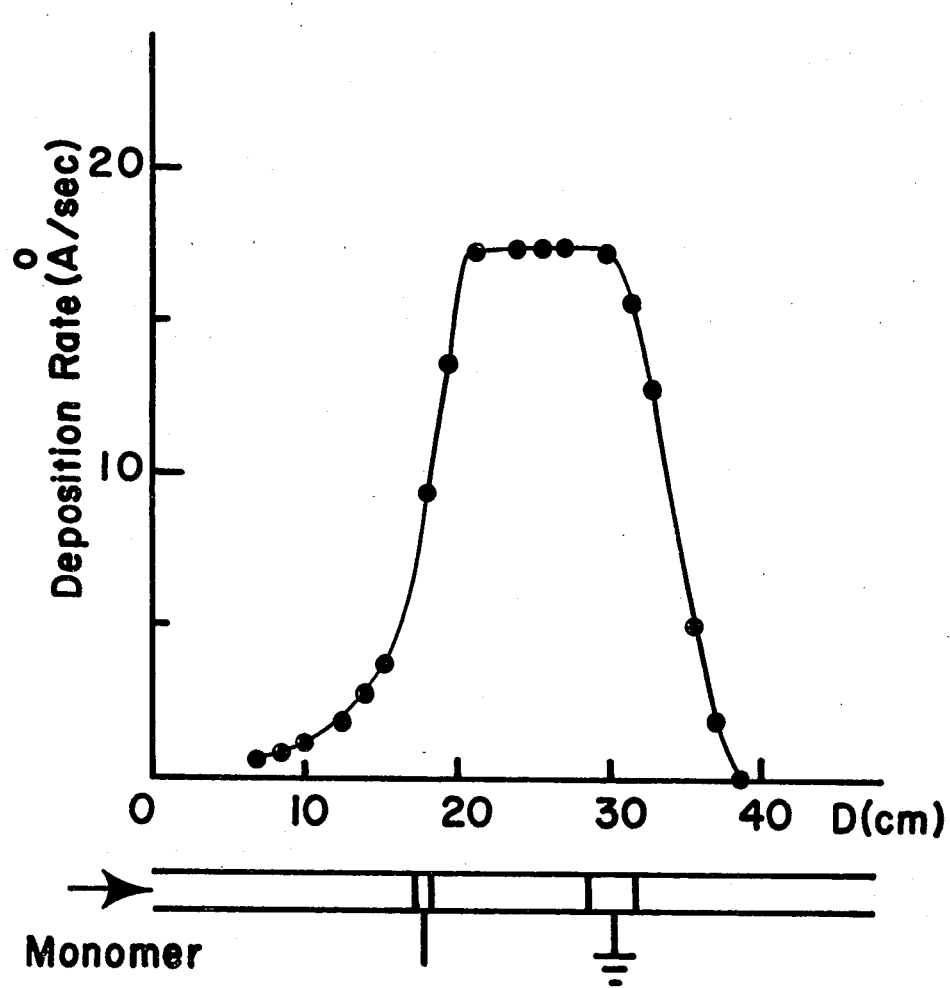
FIG. 5. A graph of the deposition rate for polypropylene.
Figure 6:
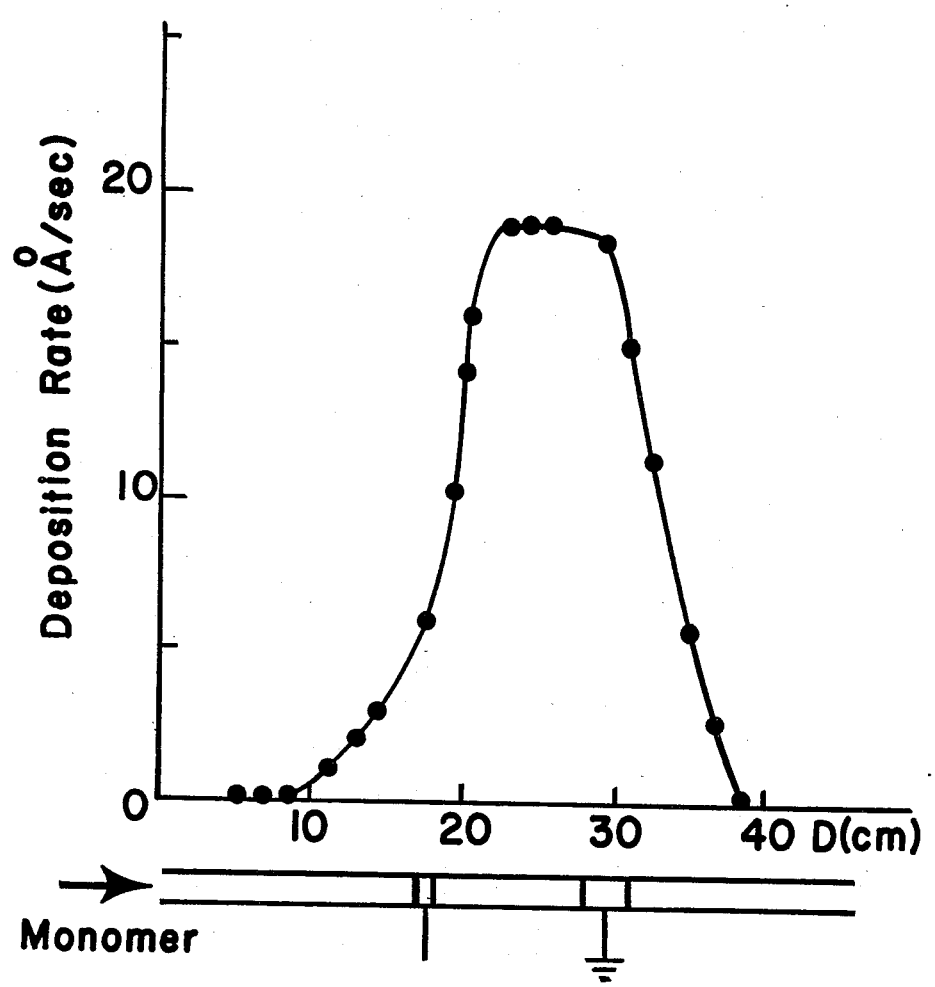
FIG. 6. A graph of the deposition rate for polypropylene admixed with nitrogen.

Tension on the substrate moving through the plasma glow zone must be kept as low as possible, to maintain the original shape and tensile strength of the substrate membrane, while allowing for proper spacing between multiple substrates and preventing the substrate from touching the wall of the reactor. Due to plasma glow zone intensity in the present system, the rate of plasma polymer deposition is much higher than possible with conventional plasma reactor systems. Plasma polymer deposition is controlled between the electrodes and "after glow" deposition is kept to a minimum. This is clearly illustrated in the graphs shown in FIGS. 5 and 6. In FIG. 5 is illustrated a graph wherein a monomer of propylene at a flow rate of 9.79 sccm, and a discharge power of 20 W attains an even plateau in the deposition rate in the area between the electrodes, the glow zone, for a normalized deposition rate of 32 Å/sec. In FIG. 6 is illustrated a graph wherein a monomer of propylene at a flow rate of 9.79 sccm, admixed with nitrogen at a flow rate of 6.70 sccm, and a discharge power of 20 W attains an even plateau in the deposition rate in the glow zone, for a normalized deposition rate of 30 Å/sec. These deposition rates were measured on glass tubes positioned within the plasma glow zone. A stationary substrate, such as this glass tube, heats up in the energy intensive glow zone and, thus, will not accept plasma polymer deposition, as well as a cooler, continuously moving substrate. Using a moving micorporous substrate according to the present invention, deposition rates approximately 2.5 times higher are achieved.

Proper spacing between the electrodes in the R.F. reactor depends on the size of the tube. In the system described here in FIG. 3, the electrodes are approximately 10–15 cm apart and the tube has a diameter of 13 mm. With larger diameter tubes, the energy density associated with the plasma glow zone should be maintained as close as possible to that in the smaller tubes reactor. Along with energy density, it is extremely important to control the monomer density. Although monomer density will generally remain the same with changes in tube size, some variation in the optimum of both energy density and monomer density will result with changes in system size and design.

Due to the extremely high energy density within the plasma glow zone, the temperature of the substrate as it moves through the plasma glow zone must be kept as low as possible (close to ambient room temperature) to insure even plasma polymer deposition rate and prevent distortion and damage to the substrate. Under normal operating conditions, some deposition of plasma polymer onto the wall of the reactor is observed. This is normally to be expected, does not deleteriously affect the process conditions, and is removed by normal routine maintainence. By keeping the substrate as cool as possible, plasma polymer will be encouraged to deposit out on the membrane substrate in preference to the walls of the reactor. Additional cooling of the substrate below room temperature may be used if desired, with the expectation that residence time in the glow zone may be increased and that plasma polymer will be further encouraged to deposit out on the membrane substrate.

A useful guide in determining changes in reaction parameters with changes in tubular geometry in an R.F. system is the composite plasma parameter, W/FM, where W is the discharge wattage, F is the flow rate of the monomer, admixed with a non-polymerizable polymerizable plasma gas if required, and M is the molecular weight of the monomer, admixed with the non-polymerizable gas if required. As the tubular geometry and system size varies, W/FM may vary for a given plasma polymer deposition rate, but optimum W/FM will not vary significantly for a given monomer system. Therefore, for a given monomer system, changes in the composite plasma parameter with changes in tubular geometry may be expressed:

$$W_1/F_1M_1 \simeq W_2/F_2M_2$$

Where $W_1/F_1M_1$ is the composite plasma parameter for a first tubular R.F. reactor as described herein, and $W_2/F_2M_2$ is the composite plasma parameter for a differently sized tubular R.F. reactor as described herein.

The advantages of the present R.F. capacitively coupled plasma polymerization reactor over conventional plasma polymerization reactor include:

1. The ability to coat both individual and plural substrates with uniformity throughout in thickness and chemical composition of the plasma polymer.

2. The ability to combine high energy densities and high deposition rates with minimum residence time for the substrate in the energy intensive plasma glow zone.

3. The ability to generate a narrower population of chemical species within the plasma glow zone than is possible in conventional plasma reactors, as evidenced by the uniform properties of the plasma polymer coatings obtained.

4. The ability to remove waste products (i.e., unreacted monomers and potentially damaging etchant gases) from the glow zone of the tubular reactor in a continuous manner, thus minimizing the effect of their presence. This is due to the fact that the monomer flow rate is faster than the speed of the substrate, allowing these waste products to be swept away. Furthermore, since the plasma polymer is almost exclusively deposited in the plasma glow zone, when the substrate moves into the "after glow" zone of the reactor, it is already protected by the deposited plasma polymer layer, which prevents possible damage from these waste products. With the system of reverse-direction motion to allow for repeatedly passing a continuous length of substrate through the glow zone, the speed of the monomer gas flow prevents "after glow" zone waste products from damaging any portion of the substrate as yet uncoated.

5. Additional advantages include the ability to manufacture composite membranes in the continuous process at rates acceptable for commercial scale production and the ability to plasma coat such sensitive substrates as polyolefins, which under conventional plasma reactor conditions, are not considered preferred membrane substrates.

FIG. 1 shows a schematic outline of a separatory module of the both end open type employing reduced pore size microporous microfiltration hollow fibers of this invention. A plurality of hollow fibers 11 is preferably used in each module unit. The hollow fibers are inserted into the module unit, which may be formed of glass or any accpetable inert material. The ends of the hollow fibers are secured within each end cap 12 of the module unit so that a liquid medium, flowing into the inlet 14a of the module unit will pass through and around the hollow fibers 11. The permeate will be collected through the outlets 13 and concentrated particulate will be withdrawn through outlet 14b. It is obvious that the inlet 14a and outlet 14b may be located at any position along the length and around the circumfence of the module unit and that there may be a plurality of inlets 14a and outlets 14b if desired.

FIG. 2 shows a schematic outline of a separatory module of the one end open type employing the reduced pore size microporous hollow fibers of this invention. A plurality of hollow fibers 21 is preferably used in each module unit. The hollow fibers are inserted into the module shell, which may be formed of glass or any acceptable inert material. The ends of the hollow fibers are secured within the end cap 22 of the module unit so that a liquid medium flowing into the inlet 24a of the module unit will pass around and through the hollow fibers 21. The permeate can be collected through outlet 23 and the concentrated particulate will be withdrawn through outlet 14b. Other suitable separatory modules according to this invention incorporating the present novel reduced pore size microporous hollow fibers are more completely described in U.S. Pat. Nos. 3,821,087, patented June 2, 1974, 3,883,393, patented May 13, 1975 and 4,184,922, patented Jan. 22, 1980, all by Knazek, et al., all of which are specifically incorporated herein by reference.

As will be obvious to those skilled in the art, the manner in which the reduced poe size microporous membranes of the present invention is employed in ultrafiltration procedures is merely a matter of choice and expediency. It need not be limited to the specific apparatus illustrated herien, but may be used in any manner which will effect the required ultrafiltration separation.

When the particles in aqueous or suitable solvent systems are plant, microbial, or mammalian cells, the modules as illustrated in FIGS. 1 and 2 provide an environment for the in vitro growth of such culturable cells, and also will provide a separating system for purifying or concentrating such cells or cellular products. When the modules as illustrated in FIGS. 1 and 2 are used for an in vitro growth environment, the cells, suspended in aqueous or suitable solvent nutrient medium are initially allowed to settle onto the outer surface of the hollow fibers through which oxygenated nutrient medium continuously flows. Nutrient substances pass from the perfusing medium through the hollow fiber wall and into the cell, while cell products pass through the hollow fiber wall and into the perfusate. These products may be recovered by suitable means. In accordance with this invention, a system may be constructed which allows at least one such culture unit, along with a nutrient medium reservoir, a gas exchanger, a pH meter and a pump to provide controlled flow rates of the perfusate. Favorable concentration gradients permit nutrients to diffuse through the walls of the hollow fibers into the cells while the products therefrom diffuse into the perfusate. A feature of these modules in addition to the growth of cells involves the retrieval from the culture of products of the cells grown on the hollow fibers while the culture itself remains undisturbed. Examples of these products include hormones, proteins and other biological substances, which in the past have been obtained from living tissue or excretory products by standard techniques. When the present modules, as illustrated in FIGS. 1 and 2, are used for the purification or concentration of cells, the mode of operation would be as described hereinabove for other types of separatory procedures. These modules may also be used for filtering pyrogens and viruses from liquids containing them. Due to the reduced size of the hollow fibers used in these modules, they are suitable for culturing, purifying or concentrating both plant, microbial, and mammalian cells and microorganisms and cellular products. Further discussion of this and other modules suitable for culturing, purifying or concentrating cells can be found more completely described in U.S. Pat. Nos. 3,821,087, patented June 28, 1974, 3,883,393, patented May 13, 1975, and 4,184,922, patented June 22, 1980, all of which are hereby incorporated specifically by reference. These modules may further serve as bio-catalytic reactors, wherein cells and enzymes are immobilized on the surface of the hollow fibers. Nutrients, chemicals and amino acids or proteins are then flowed into the module through and around the hollow fibers, contacting the immobilized cells and enzymes. Reaction with the cells and enzymes yield specialty chemicals, more complex amino acids and other cellular products of bio-therapeutic use.

PREPARATION

Polypropylene microporous hollow fibers, which have an inner diameter of 240 micrometer, a wall thickness of 24.5 micrometer and porosities of 20% and 40%, were used as substrates.

Plasma polymerization coatings were carried out according to the following conditions:

(a) Monomer: propylene 9.8 sccm
   Discharge power: 40 watts, A. F. generator (5.0 KHz)
   System pressure: 220 mtorr
   Pulling speed: varied
(b) Monomer: propylene 5.7 sccm
   Discharge power: 10-15 watts, R.F. generator (13.56 MHz)
   System pressure: P (inlet); 190 mtorr, P (outlet); 100 mtorr
   Pulling speed 2.0 cm/sec-6.5 cm/sec
(c) Monomer: 5.7 sccm+nitrogen 0.57-1.0 sccm
   Discharge power: 10-15 watts, R.F. generator (13.56 MHz)
   System pressure: P (inlet); 220 mtorr, P (outlet); 120 mtorr
   Pulling Speed: 2.0 cm/sec-6.5 cm/sec The pulling speed determines the fiber residence time in the plasma glow, with the electrodes typically spaced 15 cm apart in a tubular reactor of 13 mm diameter. The plasma polymerizate coating was deposited by passing the fiber three times through the plasma glow region. Therefore, the total effective resident distance was 45 cm.

EXAMPLE I

Microporous hollow fiber was coated by plasma polymerization according to the conditions of (a) in the preparation section, as shown in Table I. Three coating thicknesses were obtained by this preparation, 400, 800 and 1200 A. Tensile data is shown in Table II. Due to the rigid structure of the plasma coating layer, the elongation factor decreased. This rigid structure of the plasma polymerizate coating layer gives strength to the porous structure of the membrane, preventing deformation of the pores by mechanical pressure or chemical factors, and imparting long term stability. Break strength was maintained in 20% maximum decrease.

1200 A coated hollow fiber retained 90% egg albumin (MW 45,000, Eastman Kodak Co., Rochester, NY) in potassium phosphate buffer solution (pH 6.86), with a permeation rate, Ps, of $8 \times 10^{-4}$ cm$^3$/cm$^2$min. The protein concentrations were determined by liquid chromatography (Detector: UV 214 nm, Column: TSK G 2000SW, Toyo Soda Co., Japan).

TABLE I

| HOLLOW FIBERS COATED IN A.F. REACTOR | | |
|---|---|---|
| Membrane | Pulling Speed | Residence Time |
| 400 A | 53.2 cm/min. | 2.2 min. |
| 800 | 43.0 cm/min. | 4.2 min. |
| 1200 | 43.0 cm/min. | 6.2 min. |

TABLE II

| TENSILE DATA FOR COATED HOLLOW FIBER MEMBRANES | | |
|---|---|---|
| Membrane | % Elongation | Break Strength (grams) |
| Control | 194 | 223 |
| 400 A | 62 | 185 |
| 800 A | 87 | 182 |
| 1200 A | 51 | 175 |

EXAMPLE II

Reduced pore size hollow fiber membranes were prepared by plasma polymerization coating according to the conditions (b) and (c) in the preparation section, as shown in Table III. The desired coating thicknesses were obtained by controlling the residence time in the plasma glow region. Membranes having plasma polymerizate coating thicknesses of from 400 A to 1000 A were prepared. Eight separatory modules were made using the above hollow fiber membranes, each containing approximately 800 hollow fibers for a total surface area of 1000 cm$^2$. The hollow fibers used in Module 395 were prepared according to condition (b), others were prepared according to condition (c).

Ultrafiltration membrane performances were evaluated for these modules. Permeation rates are shown in Table IVa and molecular weight cutoffs are shown in Table IVb. Membrane performances varied according to the plasma polymerization coating condition, the coating thickness, and the porosity of the original microporous substrate.

The effect of plasma polymerization coating thickness is obviously demonstrated in the series of 400, 401, 413, 402 and 403. A thinner coating of plasma polymerizate gives membranes having higher water and solution permeation rates, Pw and Ps, respectively, while thicker coating gives higher retention of protein solutes, such as bovine albumin (MW 67,000) and myoglobin (MW 17,000).

The effect of surface modification to give a reduced pore size membrane having a hydrophilic surface, was carried out using a plasma gas containing 9-14% nitrogen, and the hollow fibers prepared thereby were incorporated in modules 402 and 400. Modules 400 and 402 had higher water and solution permeation rates, as compared to module 395, while maintaining high protein retention. Modules 422 and 419 were prepared using a microporous substrate of 40% porosity. Modules 422 and 419 showed higher water and solution permeation rates, as compared to module 395. These results indicate that both reduced pore size and modification of the surface of the membrane to hydrophilic were accomplished by this plasma polymerization treatment.

TABLE III

HOLLOW FIBERS COATED IN R.F. REACTOR

| Module No. | Coating Thickness | Pulling Speed | Residence Time |
|---|---|---|---|
| 400,422 | 1000 A | 2.4 cm/sec. | 18.8 sec. |
| 419 | 800 A | 3.0 cm/sec. | 15.0 sec. |
| 401,413 | 670 A | 3.6 cm/sec. | 12.5 sec. |
| 402,395 | 500 A | 4.8 cm/sec. | 9.4 sec. |
| 403 | 400 A | 6.2 cm/sec. | 7.3 sec. |

TABLE IVa

PERMEATION RATES

| Module No. | Coating Thickness (A) | Permeation Rate, $P_w$*(cm$^3$/cm$^2$ min) $\times 10^{-4}$ | Permeation Rate, $P_s$**(cm$^3$/cm$^2$ min) $\times 10^{-4}$ |
|---|---|---|---|
| (a) Porosity = 20% | | | |
| 395 | 500 | — | — |
| 400 | 1000 | 0.5 | 0.2 |
| 401 | 670 | 4.4 | 1.9 |
| 413 | 670 | 6.4 | 1.1 |
| 402 | 500 | 23.6 | 13.0 |
| 403 | 400 | 143 | 72.0 |
| (b) Porosity = 40% | | | |
| 422 | 1000 | 4.2 | 1.3 |
| 419 | 800 | 41.5 | 8.5 |

*Feed; pure water
**Feed; 100 ppm bovine albumin + 100 ppm myoglobin in 0.025 M phosphate buffer solution

TABLE IVb

MOLECULAR WEIGHT CUT-OFF

| Module No. | Retention (%) (bovine albumin) | Retention (%) (myoglobin) |
|---|---|---|
| 395 | 100.0 | 97.0 |
| 400 | 100.0 | 100.0 |
| 401 | 97.6 | 95.7 |
| 413 | 97.4 | 97.0 |
| 402 | 73.3 | 20.1 |
| 403 | 18.0 | 2.2 |
| 422 | 98.1 | 96.8 |
| 419 | 92.0 | 82.0 |

Molecular Weight:
bovine albumin; 67,000
myoglobin; 17,800

EXAMPLE III

Using modules 400, 401 and 419, which showed protein (bovine albumin) retentions of 100.0, 97.6 and 92.0% respectively, diffusion behavior was analyzed. The apparatus used was as shown in FIG. 4.

Differential pressure of extracapillary space toward the hollow fibers inside was applied, 0 psi and 1 psi. The solution in the extracapillary space was 5% bovine albumin in 0.9% NaCl aqueous solution. The solution inside the hollow fiber was 0.9% NaCl aqueous solution. The experiments were carried out at 37° C.

Diffusion behavior was analyzed in the condition of differential pressure=0 psi. The results are summarized in Table V.

Module 400 showed no solute permeation for 8 hours after the diffusion experiment was started. After 28 hours, the module maintained a high protein retention value of 99.7%.

Module 401 showed solute permeation of $4.4 \times 10^{-3}$ gram/hr in the beginning of the experiment. After 21.5 hours, the solute permeation rate decreased to $2.2 \times 10^{-3}$ gram/hr This module maintained a high protein retention of 95.6%.

Module 419 showed solute permeation of $5.9 \times 10^{-3}$ gram/hr in the beginning of the experiment. After 21.5 hours, the solute permeate rate became $4.8 \times 10^{-3}$ gram/hr. The module maintained high protein retention of 87.3%.

Diffusion analysis was also carried out in the condition of the differential pressure=1 psi. The results are summarized in Table VI.

Module 400 showed 99.3% retention and $1.1 \times 10^{-3}$ gram/hr solute permeation after 26 hours.

Module 401 showed 99.5% retention and $3.0 \times 10^{-3}$ gram/hr solute permeation after 8.1 hours.

TABLE V

DIFFUSION ANALYSIS
(Differential pressure = 0 psi)

| Time (hr) | Total Amount of solute Permeated (gram) $\times 10^{-4}$ | Solute Permeate Rate (gram/hr) $\times 10^{-4}$ | Retention (%) |
|---|---|---|---|
| Module 400 | | | |
| 4 | 0.0 | 0.0 | 100.0 |
| 8 | 0.0 | 0.0 | 100.0 |
| 20 | 7.9 | 2.2 | 99.96 |
| 24 | 20.2 | 4.0 | 99.9 |
| 28 | 49.3 | 11.0 | 99.7 |
| Module 401 | | | |
| 1.5 | 74.8 | 44.0 | 99.6 |
| 3.5 | 158 | 48.4 | 99.1 |
| 5.5 | 273 | 48.4 | 98.5 |
| 21.5 | 810 | 22.0 | 95.6 |
| Module 419 | | | |
| 1.5 | 88.0 | 59.4 | 99.5 |
| 3.5 | 242 | 110 | 98.7 |
| 5.5 | 616 | 220 | 96.7 |
| 21.5 | 2330 | 48.4 | 87.3 |

TABLE VI

DIFFUSION ANALYSIS
(Differential pressure = 1 psi)

| Time (hr) | Total Amount of solute Permeated (gram) $\times 10^{-4}$ | Solute Permeate Rate (gram/hr) $\times 10^{-4}$ | Retention (%) |
|---|---|---|---|
| Module 400 | | | |
| 4 | 0 | 0 | 100.0 |
| 5 | 1.8 | 1.8 | 99.99 |
| 6 | 3.5 | 1.8 | 99.98 |
| 7 | 5.7 | 2.2 | 99.97 |
| 24 | 106 | 8.8 | 99.4 |
| 26 | 125 | 11.0 | 99.3 |
| Module 401 | | | |
| 1 | 7.0 | 7.0 | 99.96 |
| 3.5 | 25.1 | 7.3 | 99.9 |
| 4.8 | 34.3 | 9.2 | 99.8 |
| 6 | 48.4 | 16.5 | 99.7 |
| 7.2 | 73.7 | 24.2 | 99.6 |
| 8.1 | 99.0 | 30.8 | 99.5 |

What is claimed is:

1. A microporous ultrafiltration composite membrane of reduced pore size comprising:
   a hydrophobic microporous substrate: and
   a plasma polymerizate coating on the surface of the substrate,
   the plasma polymerizate coating reducing the pore size of the microporous substrate to a size smaller than the original pore size, but not less than about 10 A, while allowing the body of the substrate to substantially retain the substrate's original properties of mechanical strength and chemical resitance.

2. A microporous ultrafiltration composite membrane of reduced pore size according to claim 1, wherein the coating is formed from the plasma polymerization of a low molecular weight aliphatic hydrocarbon monomer, and the coating imparts a hydrophobic character to the surface of the substrate.

3. A microporous ultrafiltration composite membrane of reduced pore size according to claim 1, wherein the coating is formed from the plasma polymerization of a low molecular weight aliphatic amine monomer, and the coating imparts a hydrophilic character to the surface of the substrate.

4. A microporous ultrafiltration composite membrane of reduced pore size according to claim 1, wherein the coating is formed from the plasma polymerization of a low molecular weight aliphatic hydrocarbon monomer admixed with a non-polymerizable plasma gas, and the coating imparts a hydrophilic character to the surface of the substrate.

5. A microporous ultrafiltration composite membrane of reduced pore size according to claims 1, wherein the substrate is selected from films or hollow fibers with pore sizes in the range of at least about 200 A to at most about 6000 A.

6. A microporous ultrafiltration composite membrane of reduced pore size according to claim 5, wherein the substrate is polyolefinic or fluorinated polyolefininc.

7. A microporous ultrafiltration composite membrane of reduced pore size according to claim 6, wherein the substrate is polypropylene, polyethylene or fluorinated ethylene propylene.

8. A microporous ultrafiltration composite membrane of reduced pore size according to claim 2, wherein the low molecular weight aliphatic hydrocarbon monomer is methane, ethane, ethylene, propylene, 1-butene, or 2-butene.

9. A microporous ultrafiltration composite membrane of reduced pore size according to claim 3, wherein the low molecular weight aliphatic amine is triethylamine or allylamine.

10. A microporous ultrafiltration composite membrane of reduced pore size according to claim 4, wherein the low molecular weight aliphatic hydrocarbon monomer is methane, ethane, ethylene, propylene, 1-butene or 2-butene, and the non-polymerizable plasma gas is nitrogen, oxygen or water.

11. A microporous ultrafiltration composite membrane of reduced pore size according to claim 10, wherein the non-polymerizable plasma gas is nitrogen.

12. A method of making a microporous ultrafiltration composite membrane of reduced pore size according to claim 1, comprising:
applying a radio frequency discharge to the capacitively coupled external electrodes of a tubular plasma reactor,
introducing a monomer, optionally admixed with a non-polymerizable plasma gas, into the reactor in order to energize the monomer into a plasma controlled within the glow zone between the electrodes of the reactor, and depositing a plasma polymerizate coating on the surface of a hydrophobic microporous substrate moving through the glow zone,
said plasma polymerizate coating reducing the pore size of the hydrophobic microporous substrate to a size smaller than the original pore size, but not less than about 10 A, while allowing the body of the substrate to substantially retain the substrate's original properties of mechanical strength and chemical resistance.

13. A method according to claim 12,
wherein the coating is formed from the plasma polymerization of a low molecular weight aliphatic hydrocarbon monomer, and the coating imparts a hydrophobic character to the surface of the substrate.

14. A method according to claim 12,
wherein the coating is formed from the plasma polymerization of a low molecular weight aliphatic amine monomer, and the coating imparts a hydrophilic character to the surface of the substrate.

15. A method according to claim 12,
wherein the coating is formed from the plasma polymerization of a low molecular weight aliphatic hydrocarbon monomer admixed with a non-polymerizable plasma gas, and the coating imparts a hydrophilic character to the surface of the substrate.

16. A method according to claim 13,
wherein the low molecular weight aliphatic hydrocarbon monomer is methane, ethane, ethylene, propylene, 1-butene, or 2-butene.

17. A method according to claim 14,
wherein the low molecular weight aliphatic amine monomer is triethylamine or allylamine.

18. A method according to claim 15,
wherein the low molecular weight aliphatic hydrocarbon monomer is methane, ethane, ethylene, propylene, 1-butene, or 2-butene, and the non-polymerizable plasma gas is nitrogen, oxygen or water.

19. A method according to claim 18, wherein the non-polymerizable plasma gas is nitrogen.

20. A method according to claim 12, wherein the hydrophobic microporous substrate is selected from films or hollow fibers with pore sizes in the range of at least about 200 A to at most about 6000 A.

21. A method according to claim 12, wherin the plasma reactor is adapted to process the hydrophobic microporous substrate in the form of a continuous film or hollow fiber.

22. A method according to claim 12, wherein the hydrophobic microporous substrate is a polyolefin or a fluorinated polyolefin.

23. A method according to claim 20, wherein the hydrophobic microporous substrate is polypropylene, polyethylene or fluorinated ethylene propylene.

24. A method according to claim 23, wherein the hydrophobic microporous substrate is in the form of a hollow fiber.

25. A module for separating, concentrating or purifying particulate larger than about 10 A from solutions thereof comprising:
a. a shell means having spaced end portions and defining an elongated chamber therebetween,
b. a plurality of microporous ultrafiltration hollow fibers, each of reduced pore size according to claim 1, extending in substantially parallel relationship spaced from each other within said shell means, said chamber being divided by the walls of said hollow fibers into an intracapillary space within said hollow fibers and an extracapillary space outside said hollow fibers, said intracapillary space and said extracapillary space communicating with each other only through the walls of said hollow fibers,
c. means communicating with said extracapillary space for passing solutions containing particles larger than 10 A therethrough, and d. means communicating with said intracapillary space for retrieving permeate therefrom.

26. A module according to claim 25, wherein the hollow fiber substrate is selected from polyolefins or fluorinated polyolefins wit pore sizes in the range of at least about 200 A to at most about 6000 A.

27. A module according to claim 26, wherein the hollow fiber substrate is polypropylene, polyethylene or fluorinated ethylene propylene.

28. A module according to claim 25, wherein the coating on the hollow fibers is formed from the plasma polymerization of a low molecular weight aliphatic hydrocarbon monomer, and the coating imparts a hydrophobic character to the surface of the substrate.

29. A module according to claim 25, wherein the coating on the hollow fibers is formed from the plasma polymerization of a low molecular weight aliphatic amine monomer, and the coating imparts a hydrophilic character to the surface of the substrate.

30. A module according to claim 25, wherein the coating is formed from the plasma polymerization of a low molecular weight aliphatic hydrocarbon monomer admixed with a non-polymerizable plasma gas, and the coating imparts a hydrophilic character to the surface of the substrate.

31. A module according to claim 30, wherein the non-polymerizable plasma gas is nitrogen.

32. A module according to claim 25, wherein the particulate are pyrogens or viruses.

33. A cell culture unit for the formation and maintenance of plant, microbial, or mammalian tissues in vitro comprising:
   a. a shell means having spaced end portions and defining an elongated chamber therebetween,
   b. a plurality of microporous ultrafiltration hollow fibers of reduced pore size according to claim 1, extending in substantially parallel relationships spaced from each other within said shell means, said chamber being divided by the walls of said hollow fibers into an intracapillary space within said hollow fibers and an extracapillary space outside said hollow fibers, said intracapillary space and said extracapillary space communicating with each other only through the walls of said hollow fibers, said hollow fibers being spaced from each other so a to provide sufficient extracapillary space for growth of a large number of cells, with said hollow fibers being in sufficient proximity that when the depth of cell growth on one hollow fiber is such that the cells growing on that hollow fiber farthest from that hollow fiber can no longer obtain nourishment from perfusate passing through that hollow fiber and/or removal of waste products by perfusate passing through that hollow fiber, such cells will be influenced by perfusate passing through at least one other hollow fiber,
   c. means communicating with said intracapillary space for passing perfusate therethrough, and
   d. means communicating with said extracapillary space for seeding cells and/or retrieving cells or cell products therefrom.

34. A cell culture unit according to claim 33, wherein the hollow fiber substrate is selected from polyolefins or fluorinated polyolefins with pore sizes in the range of at least about 200 A to at most about 6000 A.

35. A cell culture unit according to claim 33, wherein the hollow fiber substrate is polypropylene, polyethylene or fluorinated ethylene propylene.

36. Apparatus for the formation and maintainence of plant, microbial or mammalian cells in vitro comprising, in combination, at least one cell culture unit according to claim 33, a reservoir for perfusate, pump means, conduit means interconnecting said reservoir with said pump means and said pump means with said cell culture unit.

37. The apparatus of claim 36 including, in combination, a plurality of cell culture units.

38. The apparatus of claim 36, wherein nutrients, and amino acids or enzymes are introduced into the cell culture unit with the perfusate, allowed to react with the cells, and cellular reaction products are withdrawn therefrom.

39. A method for separating, concentrating or purifying particulate larger than about 10 A from aqueous or suitable solvent systems comprising:
   positioning a microporous ultrafiltration composite membrane of reduced pore size according to claim 1 in a suitable separatory apparatus, and
   contacting an aqueous or suitable solvent system containing particulate larger than about 10 A with said membrane,
   in order to effect the required separation, concentration or purification.

40. A method for concentrating, separating and/or purifying particulate larger than about 10 A from solutions thereof comprising:
   passing a solution containing particulate larger than about 10 A into a module according to claim 25, through means at one end of the chamber communicating with the extracapillary space in order to separate, concentrate and/or purify the particulate,
   withdrawing permeate from means communicating with the intracapillary space, and
   withdrawing separated, concentrated and/or purified particulate from means at the other end of the chamber communicating with the extracapillary space.

41. A method for the formation and maintenance of plant, microbial or mammalian tissue in vitro comprising:
   introducing living cells into the module according to claim 25 in the intracapillary space so that cells will settle onto the hollow fibers, and
   passing perfusate through the intracapillary space.

42. A microporous ultrafiltration composite membrane of reduced pore size comprising:
   a hydrophobic microporous substrate; and
   a plasma polymerizate coating on the surface of the substrate,
   the plasma polymerizate coating reducing the pore size of the microporous substrate to a size smaller than the original pore size, but not less than about 10 A,
   while allowing the body of the substrate to substantially retain the substrate's original properties of mechanical strength and chemical resistance;
   said microporous ultrafiltration composite membrane prepared by a method comprising:
   applying a radio frequency discharge to the capacitively coupled external electrodes of a tubular plasma reactor,
   introducing a monomer, optionally admixed with a non-polymerizable plasma gas, into the reactor in order to energize the monomer into a plasma controlled within the glow zone between the electrodes of the reactor, and depositing a plasma polymerizate coating on the surface of the hydrophobic microporous substrate moving through the glow zone.

43. A microporous ultrafiltration composite membrane of reduced pore size according to claim 42, wherein the coating is formed from the plasma polymerization of a low molecular weight aliphatic hydrocarbon monomer, and the coating imparts a hydrophobic character to the surface of the substrate.

44. A microporous ultrafiltration composite membrane of reduced pore size according to claim 42, wherein the coating is formed from the plasma polymerization of a low molecular weight aliphatic amine monomer, and the coating imparts a hydrophilic character to the surface of the substrate.

45. A microporous ultrafiltration composite membrane of reduced pore size according to claim 42, wherein the coating is formed from the plasma polymerization of a low molecular weight aliphatic hydrocarbon monomer admixed with a non-polymerizable plasma gas, and the coating imparts a hydrophilic character to the surface of the substrate.

46. A microporous ultrafiltration composite membrane of reduced pore size according to claim 42, wherein the substrate is selected from films or hollow fibers with pore sizes in the range of at least 200 A to at most about 6000 A.

47. A microporous ultrafiltration composite membrane of reduced pore size according to claim 46, wherein the substrate is polyolefinic or fluorinated polyolefininc.

48. A microporous ultrafiltration composite membrane of reduced pore size according to claim 47, wherein the substrate is polypropylene, polyethylene or fluorinated ethylene propylene.

49. A microporous ultrafiltration composite membrane of reduced pore size according to claim 43, wherein the low molecular weight aliphatic hydrocarbon monomer is methane, ethane, ethylene, propylene, 1-butene or 2-butene.

50. A microporous ultrafiltration composite membrane of reduced pore size according to claim 44, wherein the low molecular weight aliphatic amine is triethylamine or allylamine.

51. A microporous ultrafiltration composite membrane of reduced pore size according to claim 45, wherein the low molecular weight aliphatic hydrocarbon monomer is methane, ethane, ethylene, propylene, 1-butene or 2-butene, and the non-polymerizable gas is nitrogen, oxygen or water.

52. A microporous ultrafiltration composite membrane of reduced pore size according to claim 51, wherein the non-polymerizable plasma gas is nitrogen.

53. A module according to claim 25, wherein the particulate are plant, mammalian and microbial microorganisms, cells and cellular products.

54. A method according to claim 39, wherein the particulate are plant, mammalian and microbial microgranisms, cells and cellular products.

55. A method according to claim 40, wherein the particulate are plant, mammalian and microorganisms, cells and cellular products.

* * * * *

UNITED STATES PATENT AND TRADEMARK OFFICE
CERTIFICATE OF CORRECTION

PATENT NO. : 4,806,246
DATED : February 21, 1989
INVENTOR(S) : Hiroshi Nomura

It is certified that error appears in the above-identified patent and that said Letters Patent is hereby corrected as shown below:

Column 16, line 37, "wherin" should read -- wherein --.

Column 17, line 46, "so a to" should read -- so as to --.

Column 19, line 27, after "least" insert -- about --.

Column 20, line 30, before "microorganisms" insert -- microbial --.

Signed and Sealed this

First Day of August, 1989

Attest:

DONALD J. QUIGG

Attesting Officer

Commissioner of Patents and Trademarks